United States Patent
Kaufmann et al.

(10) Patent No.: US 10,667,933 B2
(45) Date of Patent: Jun. 2, 2020

(54) DELIVERY SYSTEM COMPRISING A SELF EXPANDING STENT

(75) Inventors: Ralf Kaufmann, Rangendingen (DE); Hardy Mueller, Bisingen (DE); Rainer Lesmeister, Reutlingen (DE); Michael Braun, Backnang (DE); John Geis, Bad Zwischenahn (DE)

(73) Assignee: JOTEC GMBH, Hechingen (DE)

(*) Notice: Subject to any disclaimer, the term of this patent is extended or adjusted under 35 U.S.C. 154(b) by 2341 days.

(21) Appl. No.: 11/391,898

(22) Filed: Mar. 29, 2006

(65) Prior Publication Data

US 2006/0247757 A1    Nov. 2, 2006

Related U.S. Application Data

(63) Continuation of application No. PCT/EP2004/010829, filed on Sep. 28, 2004.

(30) Foreign Application Priority Data

Sep. 30, 2003    (DE) ................. 103 46 200

(51) Int. Cl.
*A61F 2/95* (2013.01)
*A61F 2/966* (2013.01)
*A61F 2/82* (2013.01)

(52) U.S. Cl.
CPC .......... *A61F 2/95* (2013.01); *A61F 2002/821* (2013.01); *A61F 2002/9665* (2013.01); *A61F 2250/0018* (2013.01)

(58) Field of Classification Search
CPC ............... A61F 2/962; A61M 25/0043; A61M 25/0054
(Continued)

(56) References Cited

U.S. PATENT DOCUMENTS 5,603,710 A * 2/1997 Easley et al. ............. 606/15
5,662,703 A   9/1997 Yurek et al.
(Continued)

FOREIGN PATENT DOCUMENTS

EP    0 941 716    9/1999
EP    1 095 634    5/2001
(Continued)

OTHER PUBLICATIONS

English translation of the International Preliminary Report on Patentability for PCT/EP2004/010829, dated Aug. 31, 2006, 6 pages.
(Continued)

*Primary Examiner* — Katherine M Shi
*Assistant Examiner* — Lindsey Bachman
(74) *Attorney, Agent, or Firm* — Rimon, P.C.

(57) ABSTRACT

A delivery system is equipped with a self expanding stent for implantation into a blood vessel, in particular in the region of the aortic arch. The stent has a hollow cylindrical body which is radially compressed for implantation. A pull-back sheath which surrounds the stent and which radially compresses it is also provided for positioning and releasing the stent in the blood vessel. The pull-back sheath has a highly flexible front section which surrounds the stent and which maintains said stent in its compressed state, and has further a more rigid rear section which is connected to the front section and which is designed to transmit torsional and traction forces to the front section.

14 Claims, 4 Drawing Sheets

(58) Field of Classification Search
USPC .................................. 623/1.11; 604/525, 527
See application file for complete search history.

(56) References Cited

U.S. PATENT DOCUMENTS

| | | | |
|---|---|---|---|
| 5,899,892 A * | 5/1999 | Mortier et al. ............... | 604/523 |
| 5,976,153 A * | 11/1999 | Fischell et al. ............... | 623/1.11 |
| 6,042,588 A * | 3/2000 | Munsinger et al. .......... | 623/1.11 |
| 6,520,983 B1 * | 2/2003 | Colgan et al. ............... | 623/1.11 |
| 6,929,626 B2 * | 8/2005 | DiCarlo et al. ............... | 604/249 |
| 2003/0176910 A1 | 9/2003 | Vrba et al. | |

FOREIGN PATENT DOCUMENTS

| | | |
|---|---|---|
| EP | 1 208 816 | 5/2002 |
| WO | WO-01/34240 | 5/2001 |
| WO | WO-02/22053 | 3/2002 |

OTHER PUBLICATIONS

English translation of the claims for PCT/EP2004/010829, 2 pages.
International Search Report for PCT/EP2004/010829, dated Feb. 23, 2005, 3 pages.

* cited by examiner

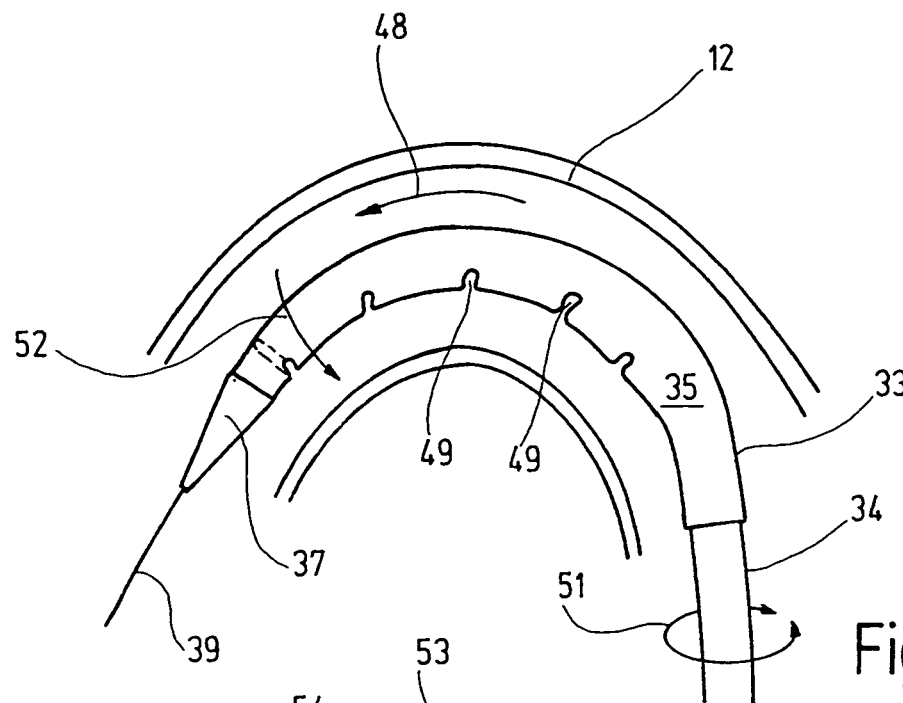
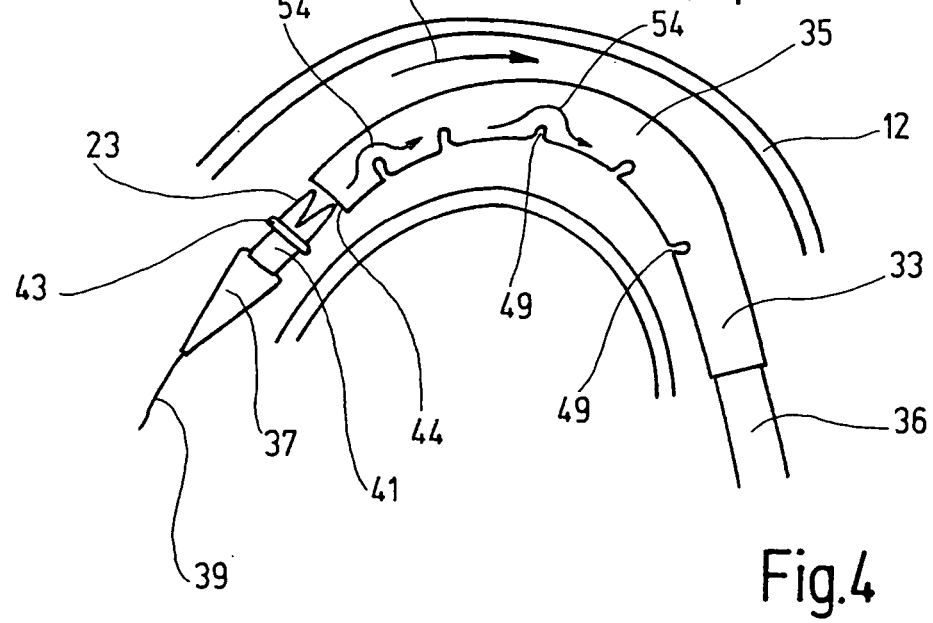

DELIVERY SYSTEM COMPRISING A SELF EXPANDING STENT

CROSS REFERENCES TO RELATED APPLICATIONS

This is a continuation application of International patent application PCT/EP2004/010829, filed Sep. 28, 2004, designating the United States and published in German as WO 2005/032423 A1, which claims priority to German application number 103 46 200.7, filed Sep. 30, 2003. The contents of these documents are incorporated herein by reference in their entirety.

BACKGROUND OF THE INVENTION

Technical Field

The present invention relates to a delivery system with a self expanding stent for implantation into a blood vessel, especially in the region of the aortic arch, said stent comprising a hollow cylindrical body which is radially compressed for implantation, and with a pull-back sheath which surrounds the stent and which radially compresses the latter for positioning and releasing the stent in the blood vessel.

Background Art

Delivery systems of this kind are used to implant endovascular stents for treatment of aneurysms in arteries. An aneurysm is understood as a widening or bulging of an arterial blood vessel as a consequence of congenital or acquired lesions of the vessel wall. The bulge can affect the vessel wall as a whole or, in what is called a false aneurysm, blood can flow from the lumen of the vessel in between the layers of the vessel wall and can tear these apart from one another. Nontreatment of an aneurysm may lead to a rupture of the artery in advanced stages, after which the patient may suffer internal bleeding.

Although aneurysms often occur in the area of the abdominal aorta (aorta abdominalis) or thoracic aorta (aorta thoracica), an aneurysm may, however, also occur in the area of the ascending or descending branch of the aorta (aorta ascendens and aorta descendens). The ascending branch of the aorta is directly connected to the heart. Starting from the aortic root (sinus aortae), the ascending branch extends upward in a slightly curved shape away from the heart and merges into the aortic arch (arcus aortae). The vessels of the head, among others the left and right carotid arteries, branch off in the area of the aortic arch. The aortic arch follows a curve of approximately 180 degrees with a very narrow radius and connects the ascending branch of the aorta to the descending branch.

The stents used for treating aneurysms of this kind comprise a hollow cylindrical metal frame whose circumferential surface is covered with a textile film or polymer film so as to provide a hollow cylindrical body. For implantation, the stent is radially compressed such that its cross-sectional surface area greatly decreases. With the aid of a delivery system, the stent is then introduced into the area of the aneurysm, where said stent is released. By virtue of the resiliency of the metal frame, the stent expands again into its original shape and thus braces its circumferential surface, the latter fastening itself in the inside of the blood vessel at positions proximal and distal to the aneurysm. In this way, the blood now flows through the stent, and further stressing of the bulge is prevented.

To obtain the desired effect of the stent, it is not only necessary to position the latter axially in such a way that it can brace itself at positions distal and proximal to the aneurysm in the relevant blood vessel; the radial orientation of the stent is often also of critical importance. This is especially the case when, at positions proximal to the aneurysm, other vessels branch off from the blood vessel affected by the aneurysm, as is the case for example in the region of the aortic arch where the arterial vessels of the head branch off. To ensure that the blood supply to these branching-off vessels is not impaired, the stents are often provided with lateral openings through which blood can pass from the interior of the stent. These openings have to be positioned in the area of the origin of the branching-off vessels, for which purpose it is necessary not only to move the stent in its longitudinal direction during its implantation, but also to rotate it about its longitudinal direction.

For implantation, these stents are radially collapsed and are then inserted into the blood vessel with the aid of intraluminally advanced catheters and positioned at the correct location in the region of the aneurysm. The correct location of the stent can be monitored via X-ray markers which are provided on the jacket of the stent, in particular in the area of the openings for supplying blood to the branching-off blood vessels.

To ensure that the stents remain in the collapsed state during the positioning procedure, they are arranged in a sheath or a tube which presses the stent radially inward. This so-called pull-back sheath is withdrawn after the stent has been positioned in the region of the aneurysm, the stent being held axially by a stop tube which is also referred to as a pusher. The pusher is in contact with the stent and maintains it in its axial position, while the pull-back sheath also surrounding the pusher is removed from the stent, the latter then expanding and bracing itself in the blood vessel.

However, the delivery systems described thus far do not work satisfactorily in those applications in which the stent has to be positioned in a curved section of a blood vessel, for example in the aortic arch.

The stents used here have particularly large dimensions; even in the radially compressed state, i.e., the collapsed state, they still have a diameter of 6 to 8 mm. The pull-back sheaths used for this consist of polymer tubes which are in most cases made from polyethylene or tetrafluoroethylene. The wall thickness of these polymer tubes is dimensioned such that it withstands the expansion pressure of the collapsed stent, remains stable over the course of time and is not subject to any thermal creep. This means, however, that the pull-back sheath has a relatively high geometric moment of inertia of its cross-sectional profile. Moreover, the pull-back sheaths are relatively rigid, so that the operating surgeon does not lose control of the degree of stent release.

If delivery systems of this kind, that is to say with radially collapsed stents placed in a rigid pull-back sheath, are implanted in narrow vessel radii, such as in the aortic arch, the pull-back sheath tend to form kinks as a result of their substantial geometric moment of inertia. One or more such kinks in the pull-back sheath then jam in the collapsed stent when an attempt is made to release it and they make it difficult or even impossible to achieve a complete release in the vessel arch at the desired location.

When delivery systems of this kind are used, the operating surgeon therefore draws the delivery system back into a distal and therefore straighter vessel region after implantation, in order to be able to release the stent there to a certain degree. Thereafter, the partially deployed stent is inserted back into the vessel arch, which is a particularly risky maneuver, as there is a danger of perforating the vessel wall. Once the stent has been correctly positioned again, it is then released completely, with considerable force being applied.

In addition to the risk of perforating the vessel wall, this maneuver often has the result that the stent cannot be positioned with adequate precision. The substantial force which has to be applied in order to overcome the kinks in the pull-back sheath also contributes to this.

DISCLOSURE OF THE INVENTION

Against this background, an object of the present invention is to make available a delivery system which is of the type mentioned at the outset and with which the aforementioned disadvantages are avoided. In particular, the novel delivery system is intended to permit a reliable positioning of the stent in the blood vessel, without the danger of the vessel wall being additionally damaged.

In the delivery system mentioned at the outset, this object is achieved by the fact that the pull-back sheath comprises a highly flexible front section which surrounds the stent and which maintains said stent in its compressed state, and further comprises a more rigid rear section which is connected to the front section and which is designed to transmit torsional and traction forces to the front section, the front and rear sections preferably being made from different materials.

The object underlying the invention is achieved in full by this means.

The inventors of the present application have in fact found that it is possible for the pull-back sheath known from the prior art to be designed as it were in two parts, where the front section, which surrounds the stent and maintains said stent in its compressed position, is of a highly flexible design, such that it is easily able to adapt to the curves of the blood vessel. Although kinks can also occur here in the tubular front section, these do not impede the withdrawal of the front section since the latter is made of highly flexible material. This material can as it were slide through the kinks and folds, and no great force is required for this purpose. The same advantages are afforded with regard to positioning in the blood vessel, since, in the event of a rotation or flexion of the highly flexible front section through the movements of the delivery system, the resulting folds or kinks uncoil very easily on the circumference and thus facilitate the positioning of the stent.

The rear section, by contrast, is made from a much stiffer material, in such a way that it is able to transmit the necessary torsional and traction forces from the actuation area outside the body, via the many decimeters of its length, to the front section of the pull-back sheath.

According to another aspect of the invention, the front and rear sections are adhesively bonded to one another.

This measure has the advantage that a reliable planar connection between the front and rear sections is created via which the corresponding forces can be transmitted.

According to a still further object, the front section comprises a textile tube, that is to say a preferably woven tube with textile structure, preferably made from a seamlessly woven textile material, more preferably from polyester material (PET).

This measure has the advantage that, for the front section of the pull-back sheath, a preferably seamlessly woven textile tube is used which, because of its textile structure, preferably its woven structure, can keep the stent radially compressed with substantial peripheral force. The textile structure at the same time ensures a low elasticity and high degree of strength in the axial tensile direction, which is of crucial advantage for the reliable positioning of the stent. Moreover, the geometric moment of inertia of the sum of all the lengthwise fibers in the cross section of the textile tube is very low, so as to afford the highly flexible properties of the front section of the pull-back sheath which, according to the invention, permit easy positioning and release of the stent.

It is true that folds and kinks also occur in a textile tube of this kind, but in the event of a rotation or flexion of the textile tube through the movements of the delivery system that are needed for positioning of the stent, these folds—so to say—uncoil very easily on the circumference, such that the positioning of the stent is not impeded. The same applies when withdrawing the textile tube from the stent after the latter has been positioned in the vessel arch, since the textile material as it were slides through the folds and kinks. The force that has to be applied to release the stent is thus reduced to that required to overcome the friction between stent and textile tube. Thus, a jamming of the stent at the folds is not possible and the stent can safely be placed in a narrow vessel arch.

According to a further aspect, the rear section comprises a traction tube which is preferably made from polymer material, in particular from polyethylene material (PE), preferably from high-density polyethylene (HDPE).

The advantage here is that the rear section of the pull-back sheath is formed by a relatively rigid traction tube which is suitable for transmitting rotational and traction forces to the textile tube. This permits reliable insertion and positioning of the stent even though the front section is made from a highly flexible material.

In an embodiment a stop tube is arranged in the rear section and abuts axially on the stent.

This measure has the advantage that the stop tube can be used for advancing the stent, such that the pushing force does not have to be exerted solely via the rear section, that is to say the traction tube. During the advancing movement, the stop tube—so to say—pushes against the distal end of the stent which, together with the front section disposed securely thereon, can thus be advanced in the blood vessel. To permit rotation of the stent, the traction tube is distorted, thereby entraining the front section and thus also the stent.

In other words, the stop tube and in addition the traction tube are principally provided for advancing the stent into the blood vessel, whereas the traction tube is provided together with the textile tube for withdrawal from the blood vessel and for rotation of the stent. A further object of the stop tube is to hold the stent in place once it is in position, whereas the traction tube is used to pull off the textile tube from the stent in the distal direction.

According to another object, the front section at the proximal end is connected in a detachable manner to a conical tip part having a soft conical tip preferably made from a soft material such as soft polyurethane (soft PU), which soft tip rests nonreleasably on a conical tip flange made from a hard material such as hard polyurethane.

The advantage of this measure is that the front or proximal end of the front section, that is to say in particular of the textile tube, is connected to a conical tip which, on the one hand, has sufficient stiffness to be advanced in a blood vessel but which, on the other hand, is sufficiently soft at the proximal end to prevent damage to the blood vessel.

Particularly in connection with this conical tip part, the use of a textile tube as the front section of the pull-back sheath is of advantage since, despite the highly flexible properties of the textile tube, the stent can be securely positioned in the blood vessel.

In one embodiment the front section is preferably shrunk thermally onto the tip flange, whereby the tip flange further preferably has, at its distal end, a circumferential bead onto which the front section is shrunk. It is also preferred if the front section lies with its front edge in a circumferential depression provided on the tip flange.

The advantage of this is that, during the advancing movement, the proximal end of the textile tube cannot inadvertently slide off and thus damage the endothelium.

It is of particular advantage if the textile tube is fixed on the tip flange by thermal shrinkage. This method makes use of the fact that textiles "contract" upon thermally overloading, the preferably rounded bead of the tip flange providing a form-fit connection to the textile tube, and this form-fit connection being such that it withstands the frictional forces arising during insertion. However, upon withdrawal of the textile tube, this form-fit connection can easily be overcome.

If the front edge of the textile tube lies in a circumferential depression provided on the tip flange, this front edge does not come into contact with the inside wall of the vessel. This on the one hand protects the endothelium, while on the other hand it prevents the textile tube from uncoiling of the tip flange.

According to another object, a guide wire catheter is provided which extends centrally through the tip part and the stent and the rear section and is connected to the tip flange for tensile load.

This guide wire catheter on the one hand serves to safely move the delivery system over a guide wire in the blood vessel. On the other hand, after the stent has been released, the guide wire catheter is used to pull the tip part back through the now expanded stent and out of the blood vessel.

Further advantages and features will become evident from the following description and from the attached drawing.

It will be appreciated that the aforementioned features and those still to be explained below can be used not only in the respectively cited combination but also in other combinations or on their own, without departing from the scope of the present invention.

BRIEF DESCRIPTION OF THE DRAWINGS

An embodiment of the invention is depicted in the drawing and is described in greater detail below with reference to the drawing, in which:

FIG. 3 shows a schematic and partially cutaway side view of the delivery system from FIG. 2 positioned in the aortic arch;

FIG. 4 shows a view like FIG. 3, but with the textile tube detached from the tip flange of the delivery system;

MODES OF CARRYING OUT THE INVENTION

Figure 1:
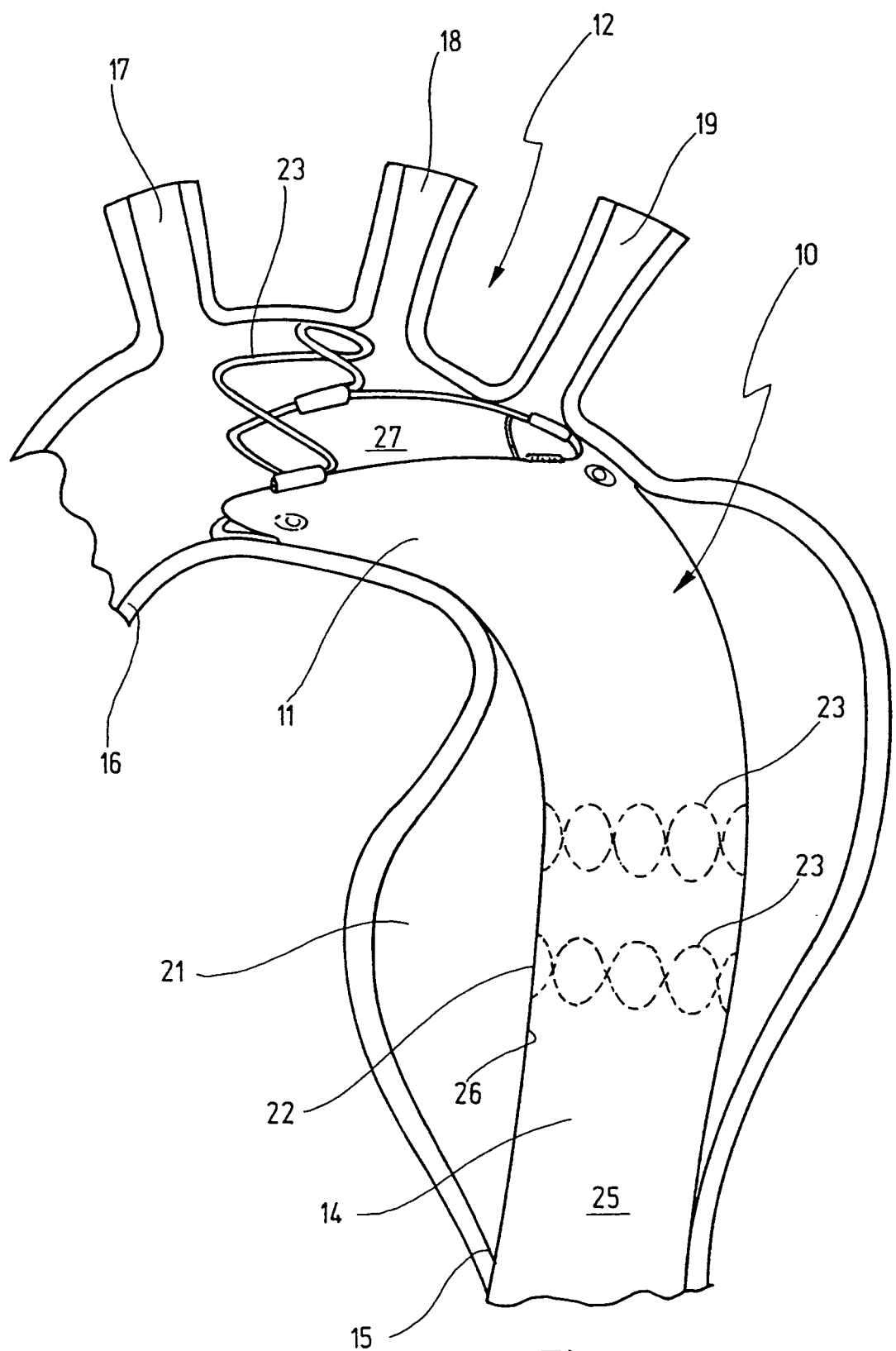
FIG. 1 shows a schematic view of an endovascular stent implanted in the region of the aortic arch.

In FIG. 1, reference number 10 designates a stent which is anchored with its proximal end 11 in the aortic arch 12 and with its distal end 14 in the descending aorta 15.

The aortic system is also shown schematically in FIG. 1 and will now first be explained in brief.

The ascending branch 16 of the aorta (aorta ascendens) is connected, via the aortic sinus (not shown in FIG. 1), to the left ventricle of the heart (also not shown in FIG. 1). The ascending aorta 16 is connected to the descending aorta 15 via the aortic arch 12. Arterial vessels of the head have their origin in the region of the aortic arch 12, namely the brachiocephalic trunk 17, the common carotid artery 18 and the left subclavian artery 19.

Reference number 21 designates an aneurysm located in the descending aorta 15 and bridged—so to say—by the stent 10. The blood flow from the ascending aorta 16 passes through the aortic arch 12 into the proximal end 11 of the stent 10 and leaves the latter at the distal end 14. For this purpose, the stent 10 has a hollow cylindrical body 22 formed by rings 23 of meandering metal supports which are indicated schematically in FIG. 1 and which are connected to one another by prosthesis material 25. The prosthesis material 25 is in a known manner a textile material or a film and is fixed to the rings 23 by sewing, gluing or melting in.

In this way, the passage through the stent 10 is kept open so that the hollow cylindrical body 22 forms with its jacket, indicated by 26.

At its proximal end 11, the stent 10 is provided with a V-shaped opening 27 which is oriented toward the arterial vessels of the head 17, 18 and 19 and through which the vessels 18 and 19 in particular are supplied with blood.

The stent 10 is self expanding, i.e., it anchors itself, by outward radial pressure, at its proximal end 11 in the aortic arch 12 and at its distal end 14 in the descending aorta 15.

Figure 2:
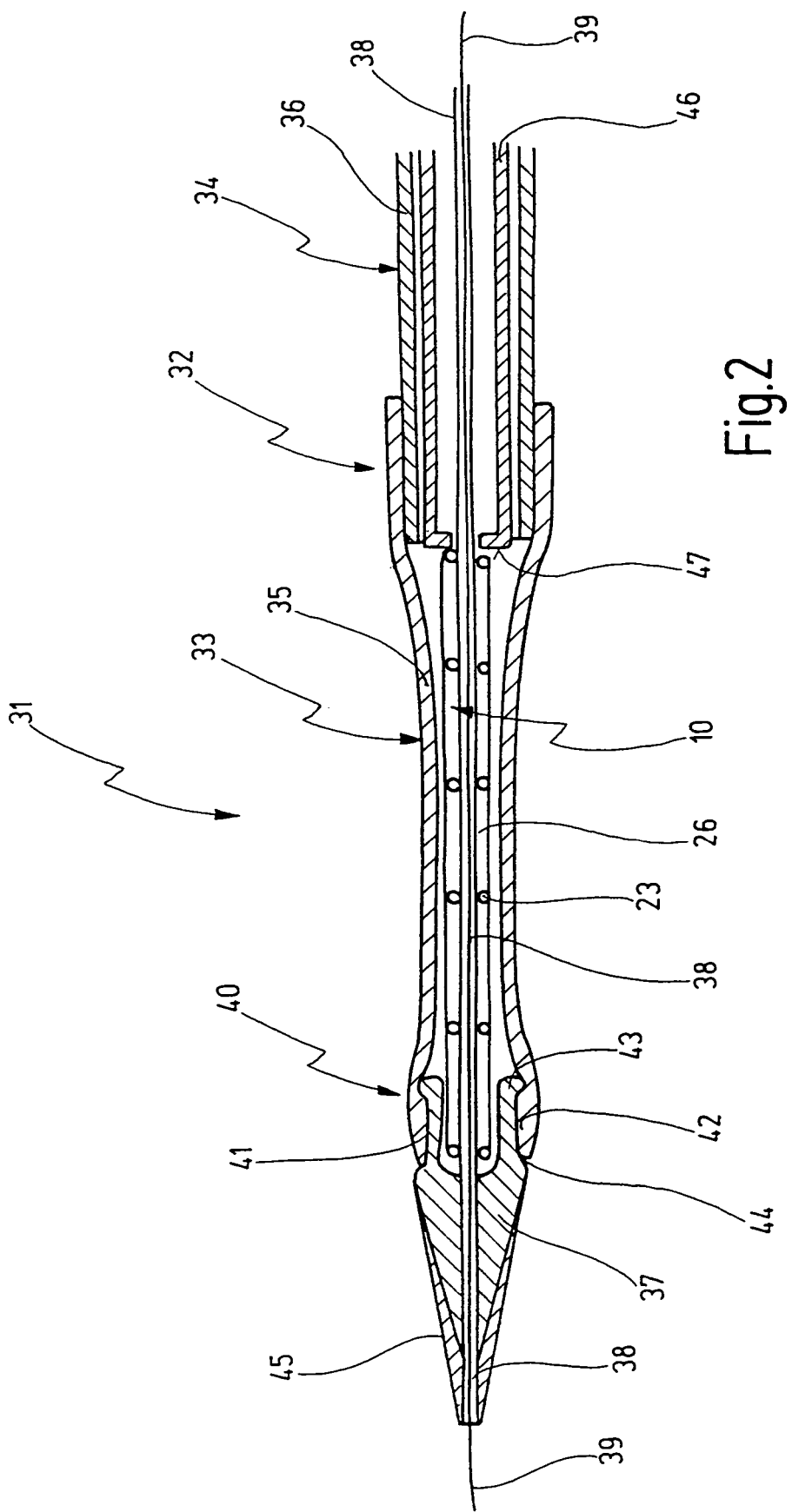
FIG. 2 shows a delivery system for placing the stent from FIG. 1 in the aortic arch and for releasing it there.

The positioning and release of the stent 10 from FIG. 1 are effected using a delivery system which is indicated by 31 in FIG. 2 and which is shown in a schematic side view and not true to scale in FIG. 2.

The stent 10 is strongly compressed radially in FIG. 2, the rings 23 and the jacket 26 being shown schematically. The stent 10 is located in a pull-back sheath 32 which has a front section 33 and a rear section 34. The front section 33, which receives the stent 10 and radially compresses it, is a textile tube 35 made from a textile material such as polyester (PET). This textile material is highly flexible due to the woven textile structure, such that the geometric moment of inertia of the sum of all the lengthwise fibers in the cross section of the textile tube 35 is very low.

The rear section 34 of the pull-back sheath 32 is a traction tube 36 made from a polymer material, for example high-density polyethylene (HDPE). The traction tube 36 is very much stiffer than the textile tube 35, with the result that it can transmit traction and rotation forces to the textile tube 35 and, via the latter, to the stent 10. For this purpose, the textile tube 35 and the traction tube 36 are adhesively bonded to one another at their overlapping seam.

A conical tip flange 37 made from a hard material, such as hard polyurethane, is arranged in the area of the proximal end 11 of the stent 10. This tip flange 37 is traversed centrally by a guide wire catheter 38, which also extends through the stent 10 and through the rear section 34 of the pull-back sheath 32, that is to say the traction tube 36. A guide wire, indicated by reference number 39, extends through the guide wire catheter 38, and the delivery system 31 is guided over the guide wire 39 in a blood vessel as it is being pushed into the latter.

At its distal end 40, the tip flange 37 comprises an annular extension 41 which has a circumferential depression 42 and, in the distal direction from the latter, a circumferential and rounded bead 43.

The textile tube 35 is pushed with its front edge 44 over the circumferential bead 43, such that the front edge 44 lies in the depression 42. The textile tube is shrunk onto the distal end 40 by heating, such that, when the delivery system 31 is pushed into a blood vessel, the textile tube 35 cannot be pushed aside from the conical tip flange 37.

A soft tip 45 made from soft polyurethane sits nonreleasably on the hard conical tip flange 37 so that, when the tip part thus comprising the tip 45 and tip flange 37 is pushed forward, the blood vessel is not internally damaged. The guide wire catheter 38 also extends through the tip 45.

In the rear section 34, that is to say in the traction tube 36, a stop tube 46 is provided whose front face 47 axially abuts against the stent 10. The stent 10 lies in turn with its proximal end 11 in the annular extension 41 and thus abuts axially against the conical tip flange 37.

To insert the stent 10 into a blood vessel, the guide wire 39, as is generally known, is first put in place, and the delivery system 31 is then pushed onto it. As the delivery system 31 is pushed forward, the front face 47 of the stop tube 46 presses against the stent 10, which with its proximal end 11 presses against the conical tip flange 37, such that the latter, and the tip 45 resting on it, are pushed forward. The textile tube 35 compresses the stent 10 radially inward, and at the same time it offers a smooth surface, such that the delivery system can be easily advanced through the blood vessel without any danger of damage to the endothelium.

Since the textile tube 35, like the stent 10, is itself highly flexible, the delivery system between the tip flange 37 and the rear section 34 of the pull-back sheath 32 also adapts to narrow radii of blood vessels, although a suitable advancing force can still be applied because the stent 10, which transmits the force from the pusher tube 46 to the tip flange 37, cannot "escape" sideways because of the textile tube 35.

The state of inserting the delivery system 31 into the aortic arch 12 is shown schematically in FIG. 3. There, reference number 48 designates the direction of insertion in which the delivery system 31 is pushed into the aortic arch 12.

To ensure that the stent 10 assumes the correct radial position in the aortic arch 12, a rotation movement indicated by 51 can be exerted via the rear section 34, this rotation movement being transmitted via the textile tube 35 to the tip flange 37 and the stent 10. Upon its advance in the direction of insertion 48, the front end of the delivery system 31 also executes a flexion movement indicated by 52, by means of which folds and kinks 49 can form in the textile tube 35.

When the stent 10 has been positioned correctly in axial and radial terms, the traction tube 36 is drawn back in the direction of a pull-off movement 53 shown in FIG. 4. The stop tube 46 remains with its front face 47 in contact with the stent 10, such that the latter does not change its axial position.

When the textile tube 35 is pulled off, it first slides with its front edge 44 over the bead 43, such that the textile tube 35 is freed from the tip flange 37. The force needed to do this can be applied to the textile tube 35 via the traction tube 36 because its elasticity in the longitudinal direction is very low and, moreover, a corresponding counterforce can be applied to the tip flange 37 via the stop tube 46 and the stent 10.

FIG. 4 shows the situation in which the textile tube 35 has just been freed from the annular extension 41 of the tip flange 37. A front ring 23 of the stent 10, however, still lies in the annular extension 41, as can be seen in FIG. 4.

Upon further withdrawal in the pull-off direction 53, the textile tube 35 now slides—so to say—through the fold 49, as is indicated by arrows 54. Catching of the textile tube 35 on the stent 10 is thus ruled out.

Figure 5:
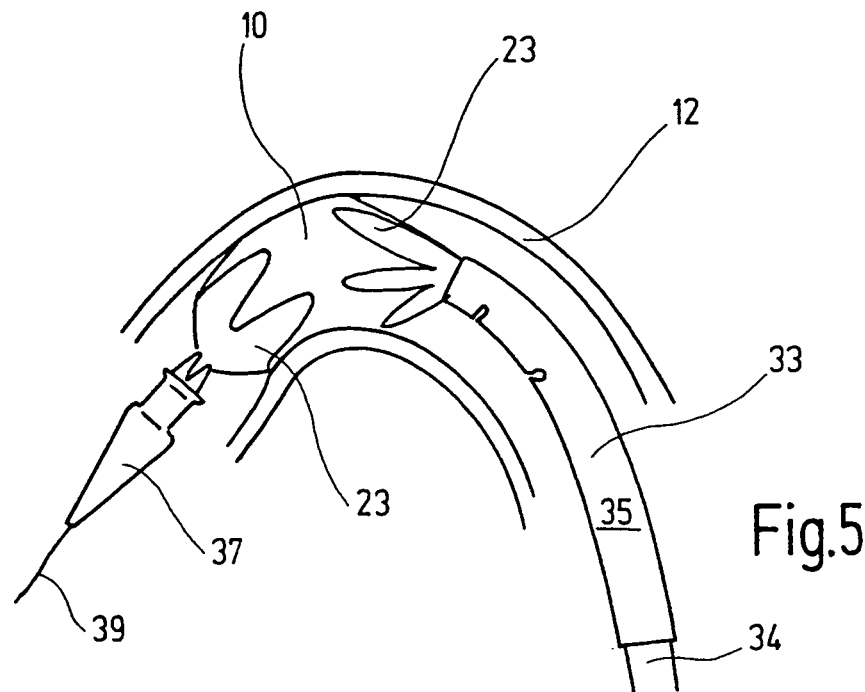
FIG. 5 shows a view like FIG. 4, but with the textile tube pulled farther back.

Upon further withdrawal of the traction tube 36 and thus of the textile tube 35, the stent 10 is released still further, as can be seen from FIG. 5 where a second ring 23 has already been freed from the textile tube 35.

Figure 6:
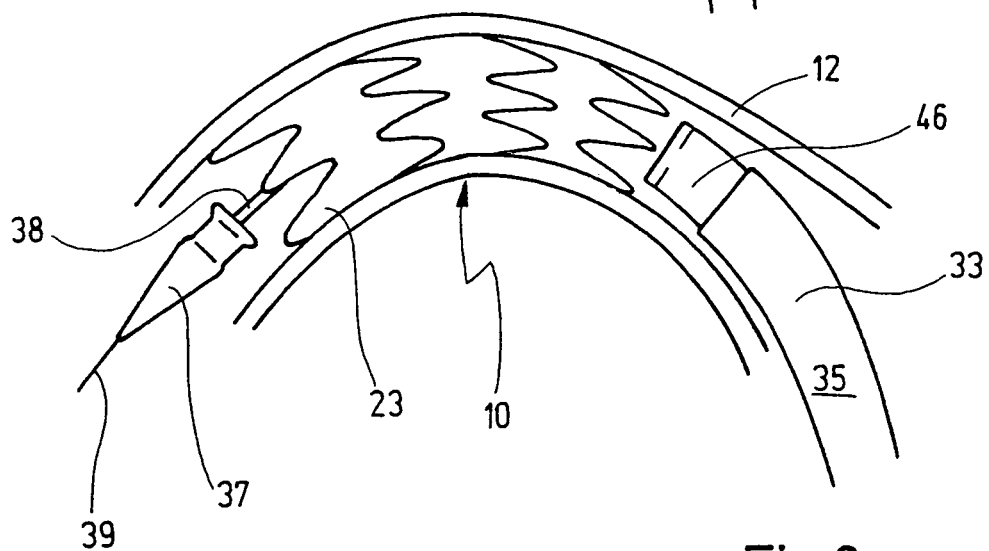
FIG. 6 shows a view like FIG. 5, but with the stent completely released, and with the tip part still lying in a position proximal to the stent.

In FIG. 6, finally, the entire stent 10 has been freed from the textile tube 35, and the front section 33 has already been partially pulled off from the stop tube 46.

The front ring 23 of the stent 10 has also now been freed from the tip flange 37, such that the latter and the tip 45 can, with the aid of the guide wire catheter 38, now be pulled through the stent 10 into the stop tube 46, before the rest of the delivery system is removed from the blood vessel.

The invention claimed is:

1. A delivery system with a self expanding stent for implantation into a blood vessel in the region of the aortic arch, said stent comprising a hollow cylindrical body which is radially compressed for implantation, and with a pull-back sheath which surrounds the stent and which radially compresses the stent for positioning and releasing the stent in the blood vessel in the region of the aortic arch, wherein the pull-back sheath comprises a highly flexible front section which surrounds the stent and which maintains said stent in its compressed state, and further comprises a more rigid rear section which is connected to the front section and which is designed to transmit torsional and traction forces to the front section, the front and rear sections being made from different materials, and wherein the front section consists of a woven textile tube with textile structure, the front section configured to form kinks and folds in the textile tube during delivery of the stent in the blood vessel in the region of the aortic arch, whereby the kinks and folds allow flexion movement during delivery of the stent in the blood vessel in the region of the aortic arch.

2. The delivery system of claim 1, wherein the front and rear sections are adhesively bonded to one another.

3. The delivery system of claim 1, wherein the textile tube is made from a seamlessly woven textile material.

4. The delivery system of claim 3, wherein the textile tube is made from polyester material (PET).

5. The delivery system of claim 1, wherein the rear section comprises a traction tube which is made from polymer material.

6. The delivery system of claim 1, wherein the front section is connected in a detachable manner to a conical tip part having a conical soft tip made from a soft material, which soft tip rests nonreleasably on a hard tip flange made from a hard material.

7. The delivery system of claim 6, wherein the front section is shrunk, thermally, onto the tip flange.

8. The delivery system of claim 6, wherein the tip flange has, at its distal end, a circumferential bead onto which the front section is shrunk.

9. The delivery system of claim 6, wherein the front section lies with its front edge in a circumferential depression provided on the tip flange.

10. The delivery system of claim 6, wherein a stop tube is arranged in the rear section and abuts axially on the stent.

11. The delivery system of claim 10, wherein a guide wire catheter is provided which extends centrally through the tip part and the stent and the rear section and is connected to the tip flange under tensile load.

12. The delivery system of claim 6, wherein a guide wire catheter is provided which extends centrally through the tip part and the stent and the rear section and is connected to the tip flange under tensile load.

13. The delivery system of claim 1, wherein a stop tube is arranged in the rear section and abuts axially on the stent.

14. The delivery system of claim 1, wherein the front section is configured to slide through the kinks and folds during a withdrawal of the stent from the blood vessel in the region of the aortic arch.

\* \* \* \* \*